(12) United States Patent
Nicolay

(10) Patent No.: US 6,767,537 B2
(45) Date of Patent: Jul. 27, 2004

(54) COMPOSITION AND METHOD FOR THE TREATMENT OF SINUSITIS

(76) Inventor: Phil Arnold Nicolay, 13141 Lowell Rd., Dewitt, MI (US) 48820

( * ) Notice: Subject to any disclaimer, the term of this patent is extended or adjusted under 35 U.S.C. 154(b) by 0 days.

(21) Appl. No.: 09/584,986

(22) Filed: May 26, 2000

(65) Prior Publication Data

US 2002/0018771 A1 Feb. 14, 2002

(51) Int. Cl.[7] .................. A01N 63/00; A01N 25/34; A61F 13/00
(52) U.S. Cl. .................. 424/93.45; 424/404; 424/434
(58) Field of Search .................. 424/93.45, 404, 424/78.02, 434; 435/853–857

(56) References Cited

U.S. PATENT DOCUMENTS

| | | | | |
|---|---|---|---|---|
| 4,298,619 A | * | 11/1981 | Mutai et al. | |
| 4,314,995 A | * | 2/1982 | Hata et al. | |
| 4,983,163 A | | 1/1991 | Winans, Jr. et al. | |
| 5,176,911 A | * | 1/1993 | Tosi et al. | |
| 5,372,810 A | | 12/1994 | Onishi et al. | |
| 5,466,463 A | | 11/1995 | Ford | |
| 5,573,765 A | | 11/1996 | Reinhard et al. | |
| 5,585,356 A | | 12/1996 | Liotta et al. | |
| 5,705,160 A | | 1/1998 | Bruce et al. | |
| 5,733,568 A | | 3/1998 | Ford | |
| 5,804,179 A | | 9/1998 | Bruce et al. | |
| 5,840,318 A | * | 11/1998 | Marshall et al. | |
| 6,156,320 A | * | 12/2000 | Izvekova et al. | |
| 6,207,703 B1 | | 3/2001 | Ponikau | |

FOREIGN PATENT DOCUMENTS

| | | | |
|---|---|---|---|
| FR | 6855 | * | 12/1967 |
| JP | 63179829 A | * | 7/1988 |
| JP | 073081851 A | * | 11/1995 |
| JP | 409002959 A | * | 1/1997 |
| JP | 40926359 A | * | 10/1997 |
| WO | WO 9942568 | * | 8/1999 |
| WO | WO 99/42568 | * | 8/1999 |

OTHER PUBLICATIONS

Moshchich et al., Pediatriia (1989); (3): 25–30. Prevention of dysbacteriosis in the early neonatal period using a pure culture of acidophilic bacteria.*

D.M. Shaw, et. al. "Engineering the microflora to vaccinate the mucosa: serum immunoglobulin G responses and activated draining cervical lymph nodes following mucosal application of tetanus toxin fragment C–expressing lactobacilli"; Immunology 100:510–518.

Buts, J.–P., "Mechanisms of Action of Biotherapeutic Agents" (web page), www.pediatrie.be/BIOTHAGT.htm, accessed Oct. 17, 2001.

Free Press news services, "Chronic sinusitus is blamed on fungus", author, date and source unknown.

Website: www.ent–consult.com/fungalsinusitis.html, "Breakthrough Discovery: Fungi are the Dominant Cause of Chronic Sinusitis", Sep. 9, 1999, Mayo Clinic Proceedings.

Website: www.smartbasics.com, MicroBac 1, Chewable Bacterial Replacement Formula information, Feb., 2000.

Fleming et al., "Role of oxidative stress in Drosphila aging.", Sep. 1992, Mutat Res, p. 267–79, from Website: www.oxis.com.

Website: www.nutritionhouse.com, information of Acidophilus and Bifidus, two pages.

Website: www.netritionals.com, "Custom Nutritional Body Support for Every Body Our Unique Approach", two pages.

Website: www.netritionals.com, information on Sinusitis, 1 page.

* cited by examiner

Primary Examiner—Christopher R. Tate
Assistant Examiner—Michele C. Flood
(74) Attorney, Agent, or Firm—Dickinson Wright PLLC; Thomas T. Moga

(57) ABSTRACT

A composition and method for the treatment of chronic sinusitis in which a composition containing desirable colonial bacteria is applied externally in the form of either a spray or a flush. The bacteria are selected from the genus Lactobacillus and the genus Bifidobacterium. The selected bacteria are provided in a therapeutically effective amount in a water solution.

5 Claims, 2 Drawing Sheets

```
┌─────────────────┐
│ PREPARATION OF  │──── 12
│ THE COMPOSITION │
└────────┬────────┘
         │
┌────────┴──────────────┐
│ BOTTLING AND SUSPENSION│──── 14
│   OF THE COMPOSITION  │
└────────┬──────────────┘
         │
┌────────┴────────┐
│ INHALATION UNTIL│──── 16
│TISSUE IS MOISTENED│
└────────┬────────┘
         │
┌────────┴────┐
│ REPEAT CYCLE│──── 18
└─────────────┘
```

COMPOSITION AND METHOD FOR THE TREATMENT OF SINUSITIS

BACKGROUND OF THE INVENTION

1. Technical Field

The present invention relates generally to ailments of the sinuses in humans. More particularly, the present invention pertains to a composition and method for the treatment of sinusitis in humans. The composition includes the bacteria *Lactobacillus acidophilus* as an anti-fungal agent in distilled water as a carrier.

2. Summary of Related Art

Formed within the bones of the human skull are four sets of open spaces which define the nasal sinuses. These spaces include a pair of frontal sinuses located above the eyes, a pair of maxillary sinuses located to either side of the nose, a pair of sphenoid sinuses located behind the bridge of the nose, and a pair of ethmoid sinuses located in the upper nose. Through the formation of a surprisingly large amount of mucous fluid (about 1 liter per day), the sinuses help to drain and continually clean the nose. The sinus membranes are lined with cilia which move in wave-like fashion and, by movement of the mucous fluid thereover, aid in the flushing and cleansing of the sinus cavities.

In their ordinary and healthy condition, the sinuses allow for the free passage of air and the equalization of air pressure. Mucous fluid flows from the sinuses and drains into the nose. However, when the passageways are obstructed, fluid cannot pass freely through the sinuses, and the sinus cavities fill with fluid and are blocked. Symptoms of sinus blockage include coughing, facial pressure, congestion, and fatigue. Sufferers of sinusitis frequently confuse sinusitis for another ailment, such as a cold, a flu, or a sore throat.

Blockage of the sinuses is typically the result of inflammation of the sinus cavities. This inflammation, known as "sinusitis," is the result of undrained mucous in one or more of the sinus cavities. There are a variety of causes of sinus inflammation, although the typical causes include the presence of fungi, bacterial and viral infection, or allergens. Other causes include obstructions due to a deviated septum and nasal polyps which form in the nasal passages and which obstruct breathing. Regardless of the cause, inflammation of the sinus cavities causes the swelling and congestion of membranes associated with the sinuses. Pain results from the congestion, mucous production increases and the mucous itself becomes thicker.

Sinusitis takes a large toll on the health of Americans and places a heavy tax on health care systems. Unexpectedly, sinusitis is more common than hypertension or arthritis. Over 500,000 visits occur annually to the emergency room by people who suffer from sinusitis.

Sinusitis may be either acute or chronic. Acute sinusitis is frequently subsequent to a cold and follows a relatively brief course of between several days and three weeks. Acute sinusitis may be caused by viral or bacterial infection of the nose, the throat, and the upper respiratory tract. A typical cause is the common cold. Antibiotics and decongestants are the medications of choice and, if regimented properly, can provide good response. Between 60% and 70% of all cases of acute sinusitis may be classified as acute.

Chronic sinusitis is defined as sinusitis lasting for more than 30 days. Bouts are frequent throughout the year. Symptoms of chronic sinusitis include runny nose, congestion, headaches, and diminished sense of smell. In addition to being of longer duration than acute sinusitis, chronic sinusitis is more difficult to treat with conventional decongestants and antibiotics. Over 40 million Americans suffer from chronic sinusitis annually.

Practitioners and researchers have traditionally believed that chronic sinusitis was generally caused by bacteriological infection. Based upon this understanding, the regimen for treatment naturally has included antibiotics. Yet success with this treatment has not been as high as for treatment of acute sinusitis, and health practitioners and researchers have long puzzled over this apparent inconsistency. Recently, however, the Mayo Clinic announced that chronic sinusitis is probably caused by fungi in the mucous of sufferers. In fact, the research showed that it was the patient's immune system response which was the cause of chronic sinusitis. For the first time, researchers now have an understanding of the reason that a regimen of antibiotics has proven largely ineffective against chronic sinusitis.

Accordingly, traditional techniques have failed to produce satisfactory results in the resolution of chronic sinusitis. An improved method of treatment remains wanting.

SUMMARY OF THE INVENTION

Accordingly, it is the general object of the present invention to provide a composition and method for treatment of chronic sinusitis.

More particularly, it is a further object of the present invention to provide such a composition and method which is directed to the regulation and limitation of the irritating fungus which is present in the sufferer's mucous.

Still a further object of the present invention is to provide such a composition and method which utilizes bacteria to re-establish a healthy, bacteria-based flora on the sinus membranes.

An additional object of the present invention is to provide such a composition and method in which the preferred bacteria are selected from the genus Lactobacillus and the genus Bifidobacterium.

Yet another object of the present invention to provide such a composition and method which is provided in the form of a spray.

Still a further object of the present invention is to provide such a composition and method which is alternatively provided in the form of a flush.

These and other objects are accomplished by the provision of a composition and method for the treatment of chronic sinusitis in which a composition containing "friendly" colonial bacteria is applied externally in the form of either a spray or a flush. The bacteria are selected from sugar-consumers which produce at least lactic acid and hydrogen peroxide as part of their end product. The lactic acid produced by the selected bacteria creates an antifungal environment which also inhibits a variety of pathogens, while the hydrogen peroxide is known to act anti-pathogenically to reduce infection. (Ironically, and with respect to the antifungal characteristics of lactic acid, the very treatment which has been traditionally used to treat chronic sinusitis—an intense regimen of antibiotics—produces the opposite result by destroying the "friendly" lactic acid-producing bacteria, thus effectively worsening the situation.)

The preferred bacteria are selected from the genus Lactobacillus and the genus Bifidobacterium. Both are anaerobic, nonsporeforming, Gram-positive rods. Both undergo fermentative metabolism in which the end product is at least partially lactic acid. A variety of members of the Lactobacillus genus are ordinarily found in the normal flora of the human mouth and intestinal tract. Bifidobacterium are ordinarily found in the intestinal tracts of babies.

Many Lactobacillus and Bifidobacterium may be used, alone or in combination.

The selected bacteria are provided in a therapeutically effective amount in a distilled water solution.

The following is a detailed description of the invention, and a summary of certain tests and results which demonstrate the effectiveness of the composition and its prescribed method of treatment.

BRIEF DESCRIPTION OF THE DRAWINGS

The present invention will be more fully understood by reference to the following detailed description of the preferred embodiments of the present invention when read in conjunction with the accompanying drawing in which:

FIG. 1 is a flow chart which demonstrates the treatment regimen in applying the composition as a spray.

DETAILED DESCRIPTION OF THE PREFERRED EMBODIMENTS

A. Introduction

Figure 2:
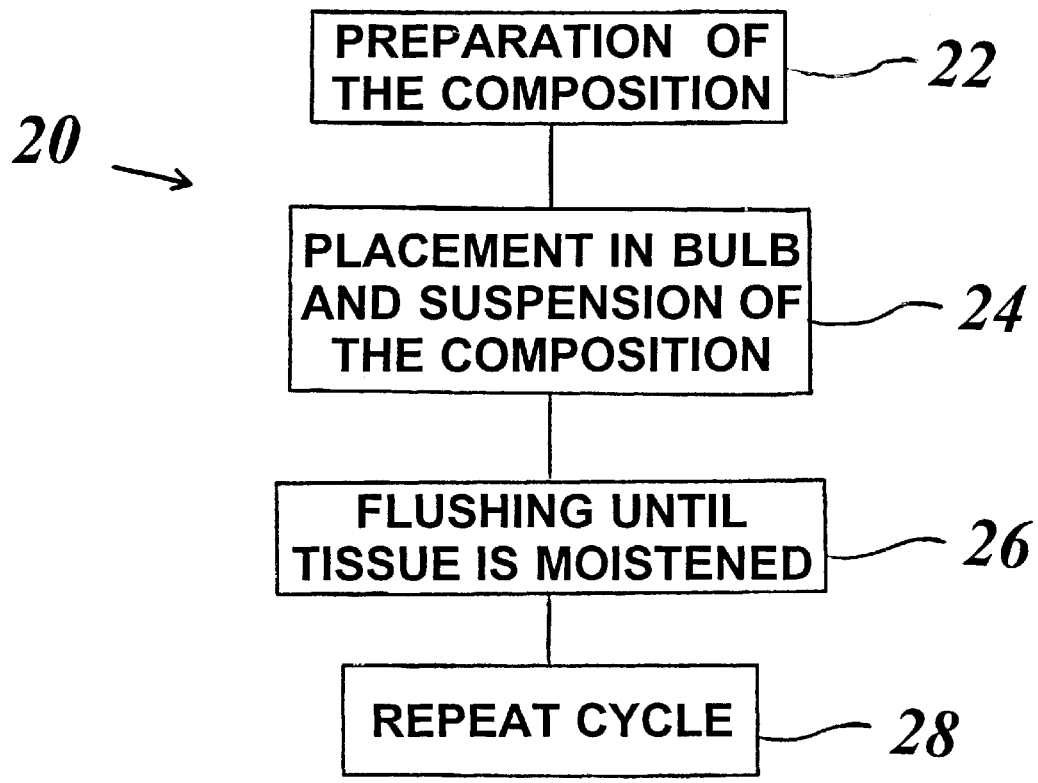
FIG. 2 is a flow chart which demonstrates the treatment regimen in applying the composition as a flush.

The composition and method of the present invention are directed to the resolution of chronic sinusitis through the use of therapeutically effective amount of bacteria provided in a neutral liquid carrier. The composition provided in accordance with the present invention contains a unique combination of a neutral liquid carrier combined with viable bacteria selected from the group consisting of one or more bacteria selected from the genus Lactobacillus and the genus Bifidobacterium.

In the preferred form of the present invention, the lactobacillus and the bifidobacterium are selected in accordance with safety and effectiveness.

In another aspect of this invention, a pharmaceutical composition and method of treatment is provided for treating chronic sinusitis in humans which comprises a safe and effective amount of one or more of the aforementioned lactobacillus and the bifidobacterium with a pharmaceutically acceptable carrier.

B. Selected Bacteria

It is preferred that the selected bacteria be drawn from bacteria of the genus Lactobacillus and/or the genus Bifidobacterium. Particularly, many types of Lactobacillus and Bifidobacterium may be used, alone or in combination. More particularly, while several members of the genus Lactobacillus and the genus Bifidobacterium may be used as part of the composition of the present invention, it is preferred that *L. casei, L. acidophilus, L. plantarum, L. fermentum, L. brevis, L. jensenii, L. crispatus, L. rhamnosus, B. longum*, and *B. breve* be used. Most particularly, the preferred Lactobacillus include *L. acidophilus* and *L. rhamnosus* while the preferred Bifidobacterium include *B. longum* and *B. breve*.

The selected variant bacteria used in the present invention can be purchased from commercial sources including, for example, Nature's Way (trademark), which provides a variety of products such as its 290 Mg capsules which contain 2.9 billion bifidobacteria and lactobacilli per capsule. Alternatively, laboratory strains could be obtained.

C. Pharmaceutically Acceptable Carrier

Insofar as the present invention is provided as a spray or, alternatively, as a flush, a water carrier is preferred. The water carrier may be either distilled, purified, or deionized water.

D. The Composition

The composition of the present invention includes one or more selected strains of bacteria and a water carrier. Each of these basic components is provided in safe and effective amounts. By "safe and effective" it is meant an amount sufficient to minimize the presence of fungi in the sinuses such that the disease state will be substantially overcome, but not so much as to cause any side effects or reactions to the composition.

Generally, a single batch of the composition preferably comprises between about 0.1 billion bacteria and about 3.0 billion bacteria to between about 15.0 mL and about 45.0 mL of the water carrier. More preferably, the composition of the present invention comprises between about 0.5 billion bacteria and about 1.5 billion bacteria to between about 20.0 mL and about 40.0 mL of the water carrier. Most preferably, the composition of the present invention comprises about 1.0 billion bacteria to about 30.0 mL of the water carrier. (Commercially available products have between about 5 billion and 10 billion microorganisms per gram. The balance of the weight is due to the inclusion of a neutral base.) Of course, these quantities may be varied depending on such variables as the intensity of the ailment, the person's age, size and sex.

The composition is created by combining the selected bacteria in the selected amount with the water carrier and mixing the composition until well-dissolved. The formed composition should be refrigerated to maintain maximum potency.

E. Methods of Use

As noted above, the composition may be used as either a spray or as a sinus flush. Once the composition is prepared as set forth above, it is ready for use. (Refrigerated mixes should be allowed to warm substantially to room temperature prior to use.)

FIGS. 1 and 2 demonstrate flow charts which define methods of use.

1. Spray Application

Referring to FIG. 1, a flow chart is disclosed which demonstrates the treatment regimen in applying the composition when applied as a spray. The method, generally illustrated as 10, includes an initial Step 12 of preparation of the composition. The composition is then placed in a spray bottle and, immediately prior to use, the user assures the existence of a mixed suspension by shaking the bottle at Step 14. With the head in the upright position, the user sprays the formula into each nostril while inhaling deeply until the sinuses are completely moistened at Step 16. (This is accomplished typically in about six spray-inhalation cycles.)

The application is made prior to sleep and should be repeated for two evenings at Step 18 for best results. One or more additional applications may be required for complete resolution. Sinusitis should be resolved within two weeks.

2. Flush Application

Referring to FIG. 2, a flow chart is disclosed which demonstrates the treatment regimen in applying the composition when applied as a flush. The method, generally illustrated as 20, includes an initial Step 22 of preparation of the composition as set forth above. The composition is then placed into a fillable ball-type syringe at Step 24. As with the use by spray, immediately prior to use, the user assures the existence of a mixed suspension by shaking the filled bulb. With the head in a downwardly-angled position (over a receptacle such as a sink), the user slowly and gently squeezes solution into each nostril until the sinuses are completely irrigated at Step 26. (This is accomplished typically in about two or three squeeze flushings.)

The application is made prior to sleep and should be repeated for two evenings at Step 28 for best results. One or more additional applications may be required for complete resolution. Sinusitis should be resolved within two weeks thereafter.

F. Example

The following is a non-limiting example set forth to illustrate the composition and method as successfully used in the treatment of chronic sinusitis. It is to be understood that this example is for illustrative purposes only and is not to be construed as limiting of the scope of the present invention.

An adult male patient was diagnosed as having chronic sinusitis. A composition was prepared through the combination of 30 mL of distilled water and one-third of a Nature's Way (trademark) 290 mg capsule, the whole capsule containing about 2.9 billion bifidobacteria and lactobacilli. Using the flushing technique outlined above, the patient repeated the regimen for two nights.

The patient's postnasal drip, sinus swelling, and thick drainage to the back of the throat were resolved within approximately two weeks after initial treatment.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. A method for treating a patient having nasal sinusitis caused by fungi, comprising the steps of:

adding between 0.5 billion and about 1.5 billion viable bacteria from one or more strains of the group consisting of *Lactobacillus acidophilus* and *L. rhamnosus* and one or more strains of the group consisting of *Bifodobacterium longum* or *B. breve* to a natural base to form part A;

measuring between about 20.0 mL and about 40.0 mL of distilled water to form part B;

combining said part A with said part B to form a composition;

mixing said composition until dissolved;

pouring an amount of said dissolved composition into a bottle for administering said composition;

applying said composition to each nostril of said patient prior to sleep with a therapeutically effective amount of said dissolved composition until the sinuses are completely irrigated;

placing said composition under refrigeration between uses;

warming and shaking said composition prior to subsequent use; and repeating the application of said composition two or more times.

2. The method according to claim 1, wherein the composition comprises a neutral base, about 1.0 billion bacteria, and about 30.0 mL of water.

3. The method according to claim 1, wherein the composition is administered by flushing.

4. The method according to claim 1, wherein the composition is administered by spraying.

5. The method according to claim 1, wherein the composition comprises *L. acidophilus*.

* * * * *

UNITED STATES PATENT AND TRADEMARK OFFICE
CERTIFICATE OF CORRECTION

PATENT NO. : 6,767,537 B2
DATED : July 27, 2004
INVENTOR(S) : Phil Arnold Nicolay It is certified that error appears in the above-identified patent and that said Letters Patent is hereby corrected as shown below:

Column 1,
Line 21, "suprisingly" should be deleted.

Column 5,
Line 12, "thereafter" should be deleted.

Column 6,
Line 8, "natural" should be -- neutral --.

Signed and Sealed this

Eighteenth Day of January, 2005

JON W. DUDAS
*Director of the United States Patent and Trademark Office*